United States Patent
Hillisch et al.

(10) Patent No.: US 7,435,757 B2
(45) Date of Patent: Oct. 14, 2008

(54) 2-SUBSTITUTED D-HOMO-ESTRA-1,3,5(10)-TRIENES AS INHIBITORS OF 17β-HYDROXY STEROID DEHYDROGENASE TYPE 1

(75) Inventors: Alexander Hillisch, Velbert (DE); Olaf Peters, Tabarz (DE); Christian Gege, Ehingen (DE); Wilko Regenhardt, Munich (DE); Gabriele Moeller, Munich (DE); Dominga Deluca, Buttapietra (IT); Jerzy Adamski, Munich (DE); Walter Elger, Berlin (DE); Birgitt Schneider, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 11/171,476

(22) Filed: Jul. 1, 2005

(65) Prior Publication Data
US 2006/0052461 A1 Mar. 9, 2006

Related U.S. Application Data

(60) Provisional application No. 60/584,475, filed on Jul. 2, 2004.

(30) Foreign Application Priority Data
Jul. 2, 2004 (DE) .................. 10 2004 032 673

(51) Int. Cl.
A61K 31/12 (2006.01)
A61K 31/56 (2006.01)
C07J 1/00 (2006.01)
C07C 49/00 (2006.01)

(52) U.S. Cl. .............. 514/680; 514/178; 514/179; 568/326; 552/502; 552/625

(58) Field of Classification Search ........... 568/326; 552/502
See application file for complete search history.

(56) References Cited

U.S. PATENT DOCUMENTS

| 3,005,835 | A | 10/1961 | Johns |
| 5,512,558 | A * | 4/1996 | Enhsen et al. ........... 514/182 |
| 6,541,463 | B1 | 4/2003 | Labrie et al. |
| 2005/0031651 | A1* | 2/2005 | Gervais et al. |

FOREIGN PATENT DOCUMENTS

| DE | 10307103 | | 2/2003 |
| WO | WO 87/00427 | * | 1/1987 |
| WO | WO 03/017973 | | 3/2003 |
| WO | WO 2004/074309 | | 9/2004 |

OTHER PUBLICATIONS

Eliseev et al., "Synthesis of racemic 2-methyl-D-homo-8-isoestrone.", Zhurnal Obshchei Khimii, vol. 57(4), 964-966, 1987, English Abstract.*
Eliseev et al., "Synthesis of steroid estrogens 8-isoanalogs with a substituent at C-2." Vestnik Leningradskogo Universiteta, Seriya 4: Fizika, Khimiya, No. 4, pp. 74-79, 1991. English Abstract.*
Zakharova et al., "Antioxidant properties of some steroids." Izvestiya Akademii Nauk SSSR, Seriya Khimicheskaya, No. 3, pp. 456-465, 1966. English Abstract.*
Egorova, V. V. et al., "Structure and reactivity of steroids. VI. Long range effects in estra—1,3,5-(10)-triene compounds," Tetrahedron, 1973, pp. 301-307 Coden: Tetrab, vol. 29, No. 2, XP002350863.

* cited by examiner

*Primary Examiner*—Barbara P Badio
(74) *Attorney, Agent, or Firm*—Millen, White, Zelano, Branigan, P.C.

(57) ABSTRACT

The invention relates to new 2-substituted D-homo-estra-1,3,5(10)-trienes of general formula I

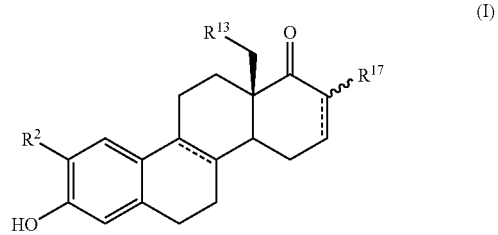

in which
$R^2$ means a $C_1$-$C_8$-alkyl group, a $C_1$-$C_8$-alkyloxy group or a halogen atom,
$R^{13}$ means a hydrogen atom or a methyl group,
$R^{17}$ means a hydrogen atom or a fluorine atom,
as well as their pharmaceutically acceptable salts,
their manufacture and use as medicaments for prophylaxis and therapy of estrogen-dependent diseases that can be influenced by inhibition of 17β-hydroxy steroid dehydro-genase type 1.

13 Claims, No Drawings

2-SUBSTITUTED D-HOMO-ESTRA-1,3,5(10)-TRIENES AS INHIBITORS OF 17β-HYDROXY STEROID DEHYDROGENASE TYPE 1

This application claims the benefit of the filing date of U.S. Provisional Application Ser. No. 60/584,475 filed Jul. 2, 2004 which is incorporated by reference herein.

This invention relates to new 2-substituted D-homo-estra-1,3,5(10)-trienes, their manufacture and use as medicaments for the treatment of estrogen-dependent diseases that can be influenced by inhibition of the 17β-hydroxy steroid dehydrogenase type 1, as well as pharmaceutical compositions that contain these compounds.

Sex hormones control the proliferation and function of steroid-sensitive normal tissue as well as malignant tissue [E. E. Baulieu, Hormones, A Complex Communication Network. In *Hormones*, eds. E. E. Baulieu and P. A. Kelly, Herman Publisher Paris and Chapman and Hall New York, 1990, pp. 147-149; D. D. Thomas, *Cancer* 53 (1984) 595-601].

Estradiol is the most active female sex hormone, which, in addition to the known effects on the reproductive system, exerts additional functions in bone and lipid metabolism and in the cardiovascular system, as well as regulatory effects in the central nervous system. It is produced primarily in the ovaries in premenopausal women. An additional large portion of the active estrogens is formed in the peripheral tissue from inactive steroid precursors, which are released into the blood in large amounts in the adrenal glands in humans.

After menopause, the estradiol level in the blood drops to about 1/10 of the content of premenopausal women [T. Thorsten, M. Tangen, K. F. Stoa, Eur. J. Cancer Clin. Oncol. 18 (1982) 333-337; A. A. van Landeghem et al., Cancer Res. 45 (1985) 2900-2906]. Starting from this time, estrogens are mainly available in the peripheral tissue via biosynthesis [F. Labrie, Intracrinology. Mol. Cell. Endocrinol. 78(1991) C113-C118].

Estrogens are taken up via the blood from tumor tissue and stimulate growth thereof.

The concentration of the intratumoral estradiol remains unchanged at a high level, however, even after menopause, comparable to that in premenopausal women [A. A. van Landeghem et al., Cancer Res. 45 (1985) 2900-2906]. The high estradiol concentration in the tumor tissue in postmenopausal women is produced by biosynthesis of estrogens in the tumor tissue.

Estradiol (E2) is formed in breast cancer tissue either via the aromatase method or the sulfatase method [Y. J. Abul-Hajj, R. Iverson, D. T. Kiang, Steroids 33 (1979) 205-222; A. Lipton et al., Cancer 59 (1987), 779-782; E. Perel et al., J. Steroid Biochem. 29 (1988) 393-399]. Androstenedione is taken up from the blood by tumor tissue, aromatized to estrone (E1) and then reduced to estradiol (E2) (aromatase method). In the sulfatase method, estrogen sulfate is converted by the steroid sulfatase into E1 and in turn reduced to E2.

The decisive last step of the steroid synthesis is catalyzed by 17β-hydroxy steroid dehydrogenases (17β-HSD), corresponding to the family of 17β-hydroxy steroid dehydrogenases/17-keto steroid reductases. These enzymes convert less active 17-keto steroids into their active 17β-hydroxy steroids and vice versa. Both estrogens and androgens show the highest affinity for the corresponding receptors in the 17β-hydroxy form, i.e., the 17β-HSD-enzymes control the biological activity of the sex hormones [H. Peltoketo et al., J. Mol. Endocrinol. 23 (1999), 1-11; P. Vihko et al., Mol. Cell. Endocrinol. 171 (2001) 71-76].

Certain extragonadal tissues such as breast and prostate tissue express reductive 17-HSDs and thus convert the precursors that circulate in the blood with low activity in the target tissues into more active forms [F. Labrie et al., Steroids 62 (1997) 148-158; H. Peltoketo et al., Horm. 55 (1999) 353-398].

Up until now, 11 different 17β-HSDs have been known. They differ in their tissue distribution, the catalytic activity, their substrate specificity, subcellular localization and by the regulation mechanism. For a large number of hydroxy steroid dehydrogenases, it was possible to show their participation in the pathogenesis of diseases of humans, for example for pseudohermaphroditism [17β-HSD 3, W. M. Geissler et al., Nat. Genet. 7 (1994) 34-39], bifunctional enzyme deficit [17β-HSD 4, E. G. van Grunsven et al., Proc. Natl. Acad. Sci. USA 95 (1998) 2128-2133], polycystic nephropathy [17β-HSD 8, M. M. Maxwell et al., J. Biol. Chem. 270 (1995) 25213-25219] and Alzheimer's disease [17β-HSD 10, S. D. Yan et al., Nature 389 (1997) 689-695; X. Y. He et al., J. Biol. Chem. 274 (1999) 15014-15019].

The human placental 17β-hydroxy steroid dehydrogenases type 1 and type 2 belong to the same Steroid Dehydrogenase-Reductase-protein family (SDR). They are distinguished from one another by, i.a., the direction of reaction, which is catalyzed by the enzymes.

17β-HSD 1 primarily controls the reduction of estrone to estradiol [T. Puranen et al., Endocrinology 138 (1997) 3532-3539] with participation by NADPH as a co-factor [J. Z. Jin, S. X. Lin, Biochem. Biophys. Res. Commun. 259 (1999) 489-493].

In cultivated cells, the HSD 1 partially supports the reduction of androstenedione and androstanedione. It could clearly be shown, however, that phenolic substrates are preferred [M. Poutanen et al., Endocrinology 133 (1993) 2639-2644].

In comparison to 17β-HSD 1, however, the 17β-HSD 2 catalyzes the opposite reaction, namely the conversion of estradiol to estrone and of androstenedione and dihydrotestosterone to androstanedione [L. Wu et al., J. Biol. Chem. 268 (1993) 12964-12969] and preferably acts in the presence of the non-phosphorylated form of the co-factor NAD [F. Labrie et al., Steroids 62 (1997) 148-158].

17β-HSD 1 and 2 are expressed in normal mammary gland tissue [G. Söderqvist, J. Clin. Endocrinol. Metab. 83 (1998) 1190-1193; M. Miettinen, Breast Cancer Res. Treat. 57 (1999) 175-182].

In contrast to the normal breast tissue, the reductive activity (by 17β-HSD 1) in malignant breast epithelial cells is found to be increased compared to the oxidative activity (by 17β-HSD 2) [M. M. Miettinen et al., Biochem. J. 314 (1996) 839-845; V. Speirs, J. Steroid Biochem. Mol. Biol. 67 (1998) 267-274]. It was observed that estradiol is accumulated in malignant breast cells, which also points to an activity of 17β-HSD 1 [A. Vermeulen et al., Eur. J. Cancer Clin. Oncol. 22 (1986) 515-525]. In addition, it was found that in the presence of 17β-HSD 1, the administration of estrone leads in the same way to a growth of breast cancer cells just like the administration of estradiol by itself. In contrast to this, the administration of estrone by itself without 17β-HSD 1 does not produce this effect [M. M. Miettinen et al., Int. J. Cancer 68 (1996) 600-604].

The dominance of 17β-HSD 1 in malignant tissue results in increased estrogen-dependent growth and progress of tumors, while the oxidative 17β-HSD 2 protect normal breast tissue cells from an excessive estradiol effect [P. Vihko et al. Mol. Cell. Endocrinol. 171 (2000) 71-76].

In the case of endometriosis, the equilibrium between 17β-HSD 1 and 2 plays a role. 17β-HSD 1 is expressed in eutopic tissue, but the hormone-inactivating enzyme 17β-HSD 2 is completely lacking [S. E. Bulun et al. J. Mol. Endocrinol. 25 (2000) 35-42.]

Also, in the case of prostate cancers, 17β-HSD 2 is reduced [J. P. Elo et al., Endocrinol. Metab. 88 (2003) 705-712].

Among the previously developed 17β-HSD 1 inhibitors, the irreversible inhibitors are distinguished from the reversible inhibitors. The irreversible inhibitors contain a reactive functional group, which inactivates the latter by forming a covalent bond with an amino acid radical of the enzyme. Known representatives of the above-mentioned group are 16-methylene-estradiols, acetylene-substituted 16-seco-estradiol [R. J. Auchus, D. F. Covey, Biochemistry 25 (1983) 7295-7300; J. L. Thomas et al., J. Biol. Chem. 258 (1983) 11500-11504; B. Tobias et al., J. Biol. Chem. 257 (1982) 2783-2786] or else 16α-haloalkyl-estradiols [K. M. Sam et al., Drug Des. Discov. 15 (1997) 157-180; M. R. Tremblay, D. Poirier, J. Steroid Biochem. Mol. Biol. 66 (1998) 179-191].

The reversible inhibitors include 16,17-pyrazole- or 16,17-isoxazole-estrone derivatives [F. Sweet et al. Biochem. Biophys. Res. Commun. 180 (1991), 1057-1063], estradiol derivatives with a long 7α-undecanamide side chain [C. Labrie et al. *Cancer Res.* 52 (1992), 610-615; S. J. Santner, R. J. Santen, J. Steroid Biochem. Mol. Biol. 45 (1993) 383-390] or with a 6β-thiaheptanamide side chain [D. Poirier, P. Dionne, S. Auger, J. Steroid Biochem. Mol. Biol. 64 (1998), 83-90].

A special case as a 17β-HSD 1-inhibitor is the 16-oxoestrone: at a neutral pH of 7.2, it includes the reversible inhibitors, and under basic conditions at a pH of 8.5, it includes the irreversible inhibitors [H. Inano, B. Tamaoki, Eur. J. Biochem. 129 (1983) 691-695].

The previously known, both reversible and irreversible inhibitors have only one moderate activity as 17β-HSD 1 inhibitors.

The first hybrid inhibitor was recently found by modeling studies [M. Tremblay, D. Poirier et al., FASEB 13 (2002) 1829-1831]. The hybrid inhibitor, in which estradiol is linked to adenosine via a spacer that consists of 8 methylene groups at 16-position, inhibits the 17β-HSD 1 as the best inhibitor to date with an $IC_{50}$ value of 52 nmol.

Because of the size of this molecule, making this compound bioavailable orally would be difficult. It is not unlikely that the molecule undergoes a cross reaction with other NAD (P)(H)-dependent enzymes.

From the known prior art, 17β-HSD 1 is a target for local inhibition of the estradiol biosynthesis. Accompanying treatment with antihormones, which are to prevent the binding of the active steroid to the corresponding receptor, 17β-HSD 1 inhibitors can be used to support treatment of estrogen-dependent diseases.

The object of this invention is therefore to provide additional compounds that inhibit the 17β-HSD 1 selectively. These compounds are to be suitable for treating estrogen-dependent diseases as well as hormone-dependent tumor diseases, which can be influenced by inhibition of the 17β-hydroxy steroid dehydrogenase type 1.

Additional subjects of this invention are the production and use of these compounds as pharmaceutical agents for treating estrogen-dependent diseases as well as hormone-dependent tumor diseases, which can be influenced by inhibition of 17β-hydroxy steroid dehydrogenase type 1.

The object is achieved according to this invention by the provision of new 2-substituted D-homo-estra-1,3,5(10)-trienes of general formula I

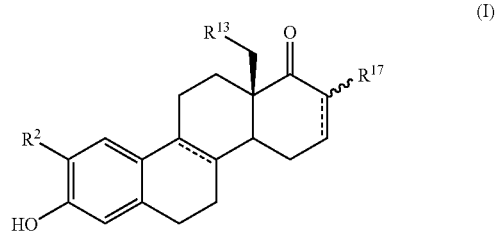

in which
R² means a saturated or unsaturated $C_1$-$C_8$-alkyl group, an aralkyl or an alkylaryl radical, a $C_1$-$C_8$-alkyloxy group or a halogen atom,
R¹³ means a hydrogen atom or a methyl group,
R¹⁷ means a hydrogen atom or a fluorine atom, whereby the dotted lines in the B- and D-ring of the steroid molecule can be additional double bonds, as well as their pharmaceutically acceptable salts.

In addition, this invention comprises the new compounds as pharmaceutical active ingredients, their production, their therapeutic application and pharmaceutical dispensing forms that contain the new substances.

The compounds of general formula (I) according to the invention or their pharmaceutically acceptable salts can be used for the production of a pharmaceutical agent, in particular for treating estrogen-dependent diseases as well as hormone-dependent tumor diseases that can be influenced by inhibition of the 17β-hydroxy steroid dehydrogenase type 1.

It was determined that the low-molecular 2-substituted D-homoestra-1,3,5(10)-trienes according to the invention produce a selective inhibition of the 17β-HSD 1-enzyme activity in vitro that is stronger than the previously known 17β-HSD 1 inhibitors.

Unless further specified otherwise, for the purposes of this invention this is an aryl radical that optionally can be substituted by a phenyl, 1- or 2-naphthyl radical, whereby the phenyl radical is preferred. Unless expressly indicated otherwise, aryl also always includes a heteroaryl radical. Examples of a heteroaryl radical are the 2-, 3-, or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2,4- or 5-pyrimidinyl radical or the 3- or 4-pyridazinyl radical.

As substituents for an aryl or heteroaryl radical, for example, a methyl, ethyl, trifluoromethyl, pentafluoroethyl, trifluoromethylthio, methoxy, ethoxy, nitro, cyano, halogen (fluorine, chlorine, bromine, iodine), hydroxy, amino, mono ($C_{1-8}$-alkyl) or di($C_{1-8}$-alkyl)amino, whereby both alkyl groups are identical or different, di(aralkyl)amino, whereby both aralkyl groups are identical or different, can be mentioned.

The $C_1$-$C_8$-alkyl groups for R² can be saturated or unsaturated and can be partially or completely substituted. As representatives of the saturated alkyl radicals, a methyl, ethyl, n-propyl-, iso-propyl-, n-, iso-, or tert.-butyl, n-, iso- or neo-pentyl group, hexyl, heptyl or octyl can be mentioned. Methyl, ethyl and propyl are preferred.

Allyl and vinyl stand as representatives for unsaturated alkyl radicals.

A methoxy, ethoxy, n-propoxy, iso-propoxy, n-, iso-, or tert.-butoxy, n-, iso- or neo-pentoxy group can stand for the $C_1$-$C_5$-alkoxy radical R².

In the case of $R^2$, a chlorine, iodine or bromine atom can stand for a halogen.

Preferred according to this invention are compounds of general formula I, in which $R^2$ is a $C_1$-$C_5$-alkoxy, $C_1$-$C_5$-alkyl or $C_2$-$C_3$-alkenyl or bromine, or chlorine, and $R^{13}$ is a hydrogen atom.

The compounds that are mentioned below and use thereof are preferred according to the invention:
1) 2-Methoxy-17a-oxo-17a-homoestra-1,3,5(10)-trien-3-ol 1
2) 2-Ethoxy-17a-oxo-17a-homoestra-1,3,5(10)-trien-3-ol
3) 2-Chloro-17a-oxo-17a-homoestra-1,3,5(10)-trien-3-ol 2
4) 2-Bromo-17a-oxo-17a-homoestra-1,3,5(10)-trien-3-ol 3
5) 2-Iodo-17a-oxo-17a-homoestra-1,3,5(10)-trien-3-ol 4
6) 2-Chloro-17α-Fluoro-17a-oxo-17a-homoestra-1,3,5(10)-trien-3-ol 5a
7) 2-Chloro-17β-Fluoro-17a-oxo-17a-homoestra-1,3,5(10)-trien-3-ol 5b
8) 2-Bromo-17β-Fluoro-17a-oxo-17a-homoestra-1,3,5(10)-trien-3-ol
9) 2-Bromo-17β-Fluoro-17a-oxo-17a-homoestra-1,3,5(10)-trien-3-ol
10) 2-(2-Phenylethyl)-17a-oxo-17a-homoestra-1,3,5(10)-trien-3-ol 6
11) 2-Allyl-17a-oxo-17a-homoestra-1,3,5(10)-trien-3-ol 7
12) 2-Allyl-17α-Fluoro-17a-oxo-17a-homoestra-1,3,5(10)-trien-3-ol
13) 2-Allyl-17β-Fluoro-17a-oxo-17a-homoestra-1,3,5(10)-trien-3-ol
14) 2-Chloro-17a-oxo-17a-homoestra-1,3,5(10),16-tetraen-3-ol
15) 2-Bromo-17a-oxo-17a-homoestra-1,3,5(10),16-tetraen-3-ol 8
16) 2-Allyl-17a-oxo-17a-homoestra-1,3,5(10),16-tetraen-3-ol
17) 2-Propyl-17a-oxo-17a-homoestra-1,3,5(10)-trien-3-ol
18) 2-Methoxy-17a-oxo-17a-homo-18a-homoestra-1,3,5(10)-trien-3-ol
19) 2-Ethoxy-17a-oxo-17a-homo-18a-homoestra-1,3,5(10)-trien-3-ol
20) 2-Chloro-17a-oxo-17a-homo-18a-homoestra-1,3,5(10)-trien-3-ol
21) 2-Bromo-17a-oxo-17a-homo-18a-homoestra-1,3,5(10)-trien-3-ol
22) 2-Iodo-17a-oxo-17a-homo-18a-homoestra-1,3,5(10)-trien-3-ol
23) 2-Chloro-17α-Fluoro-17a-oxo-17a-homo-18a-homoestra-1,3,5(10)-trien-3-ol
24) 2-Chloro-17β-Fluoro-17a-oxo-17a-homo-18a-homoestra-1,3,5(10)-trien-3-ol
25) 2-Bromo-17α-Fluoro-17a-oxo-17a-homo-18a-homoestra-1,3,5(10)-trien-3-ol
26) 2-Bromo-17β-Fluoro-17a-oxo-17a-homo-18a-homoestra-1,3,5(10)-trien-3-ol
27) 2-Allyl-17a-oxo-17a-homo-18a-homoestra-1,3,5(10)-trien-3-ol
28) 2-Allyl-17α-Fluoro-17a-oxo-17a-homo-18a-homoestra-1,3,5(10)-trien-3-ol
29) 2-Allyl-17β-Fluoro-17a-oxo-17a-homo-18a-homoestra-1,3,5(10)-trien-3-ol
30) 2-Chloro-17a-oxo-17a-homo-18a-homoestra-1,3,5(10),16-tetraen-3-ol
31) 2-Bromo-17a-oxo-17a-homo-18a-homoestra-1,3,5(10),16-tetraen-3-ol
32) 2-Allyl-17a-oxo-17a-homo-18a-homoestra-1,3,5(10),16-tetraen-3-ol
33) 2-Propyl-17a-oxo-17a-homo-18a-homoestra-1,3,5(110)-trien-3-ol Pharmacological Data Inhibition of the Activity of Human 17β-Hydroxy Steroid Dehydrogenase Type 1

The test process is well described in the literature [Adamski, J., Sierralta, W. D., Jungblut, P. W., Acta Endocrinol (Copenh.) 121(2) (1989), 161-7] and is depicted below.

Human 17β-hydroxy steroid dehydrogenases (17β-HSDs) are over-expressed in *E. coli* bacteria as His-Tag proteins or as GST-fusion proteins. The suspensions of the bacterial pellets in isotonic common salt solution are used for the determination of enzyme activities of the 17β-HSDs or for the study of their influence by potential inhibitors (estrogen derivatives).

The measurements are made in double determination and, if necessary, at various concentrations of potential inhibitors (e.g., in determining the $IC_{50}$ values). In addition to the target enzyme 17β-HSD 1, other steroid-metabolizing enzymes are included in the test to study cross reactivities of estrogen derivatives.

$^3$H-Labeled substrate, bacterial suspensions, DMSO (in the control batch; final 1%) or the potential inhibitors (estrone derivatives in DMSO) as well as suitable cofactors (NADP (H) or NAD(H); 5 mg/ml in $H_2O$) are added to a defined volume of 100 mmol of sodium phosphate buffer. The incubation of the samples is carried out at 37° C. in a water bath while being shaken, such that in the control (without substances to be tested), a conversion of about 30% is achieved.

The separation of radiolabeled substrate and product is then carried out, after extraction with 1 ml of reversed phase-(RP-18)-cartridges, by means of HPLC on an RP18 column with acetonitrile:water 1:1 (v/v) as a mobile phase. The radioactivity is detected with the aid of a flow-scintillation counter.

The evaluation of the substrate conversion with and without substances to be tested is performed by the integration of the substrate and product peaks. The conversion of the control is normalized to 100% conversion.

TABLE 1

Inhibition of the Human 17β-Hydroxy Steroid Dehydrogenase

| Structure | 17βHSD1 $IC_{50}$ [nmol] |
| --- | --- |
| 1 | 85 |
| 2 | 77 |
| 3 | 52 |
| 4 | 52 |
| 5a | 87 |
| 5b | 126 |
| 6 | 15 |
| 7 | 24 |
| Estrone | 109 |

Dosage

In general, satisfactory results in the treatment of estrogen-dependent diseases as well as hormone-dependent tumor diseases can be expected if the daily doses encompass a range of 5 μg to 50 mg of the compound according to the invention per kg of body weight. In the case of larger mammals, for example humans, a recommended daily dose lies in the range of 10 μg to 30 mg per kg of body weight.

Suitable dosages for the compounds according to the invention are from 0.005 to 50 mg per day per kg of body weight, depending on the age and constitution of the patient, whereby the necessary daily dose can be administered one or more times.

The formulation of the pharmaceutical preparations based on the new compounds is carried out in a way that is known in the art by the active ingredient being processed with the vehicles, fillers, substances that influence decomposition, binding agents, moisturizers, lubricants, absorbents, diluents, taste corrigents, coloring agents, etc., that are commonly used in galenicals, and converted into the desired form of administration. In this case, reference is made to Remington's Pharmaceutical Science, 15$^{th}$ Ed., Mack Publishing Company, East Pennsylvania (1980).

For oral administration, in particular tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local therapy.

For pulmonary administration of the new compounds, the latter can be used in the form of aerosols and inhalants.

For topical application, formulations in gels, ointments, fatty ointments, creams, pastes, powders, milk and tinctures are possible. The dosage of the compounds of general formula I should be 0.01%-20% in these preparations to achieve an adequate pharmacological action.

This invention comprises the compounds of general formula I as well as use thereof for the production of a pharmaceutical agent, in particular for treating estrogen-dependent diseases, which can be positively influenced by the inhibition of the 17β-hydroxy steroid dehydrogenase.

The compounds of general formula I according to the invention are preferably used for the production of a pharmaceutical agent for treating hormone-dependent tumor diseases of male and female reproductive glands, male and female sex organs including the mammary glands, in particular prostate cancers or breast cancers.

In addition, the compounds according to the invention for the production of a pharmaceutical agent for treating endometriosis are preferred.

This invention also relates to the pharmaceutical compositions that contain at least one compound according to the invention, optionally in the form of a pharmaceutically/pharmacologically compatible salt, without or together with pharmaceutically compatible adjuvants and/or vehicles.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one compound according to the invention.

The pharmaceutical agents of the invention are produced with commonly used solid or liquid vehicles or diluents and the commonly used pharmaceutical-technical adjuvants corresponding to the desired type of administration with a suitable dosage in a known way. The preferred preparations consist in a dispensing form that is suitable for oral administration. Such dispensing forms are, for example, tablets, film tablets, coated tablets, capsules, pills, powders, solutions or suspensions or else depot forms.

The pharmaceutical compositions that contain at least one of the compounds according to the invention are preferably administered orally.

Parenteral preparations, such as injection solutions, are also considered. In addition, for example, suppositories and agents for vaginal application can also be mentioned as preparations.

Corresponding tablets can be obtained by, for example, mixing the active ingredient with known adjuvants, for example inert diluents, such as dextrose, sugar, sorbitol, mannitol, polyvinylpyrrolidone, explosives such as corn starch or alginic acid, binding agents such as starch or gelatin, lubricants such as magnesium stearate or talc and/or agents for achieving a depot effect, such as carboxylpolymethylene, carboxyl methyl cellulose, cellulose acetate phthalate or polyvinyl acetate. The tablets can also consist of several layers.

Coated tablets can accordingly be produced by coating cores, which are produced analogously to the tablets, with agents that are commonly used in tablet coatings, for example polyvinylpyrrolidone or shellac, gum arabic, talc, titanium oxide or sugar. In this case, the coated tablet shell can also consist of several layers, whereby the adjuvants that are mentioned above with the tablets can be used.

Solutions or suspensions of the compounds of general formula I according to the invention can additionally contain taste-improving agents, such as saccharine, cyclamate, or sugar, as well as, e.g., flavoring substances such as vanilla or orange extract. In addition, they can contain suspending adjuvants, such as sodium carboxymethyl cellulose, or preservatives, such as p-hydroxybenzoates.

The compounds of general formula I that contain capsules can be produced by, for example, the compound(s) of general formula I being mixed with an inert vehicle such as lactose or sorbitol and being encapsulated in gelatine capsules.

Suitable suppositories can be produced by, for example, mixing with vehicles that are provided for this purpose, such as neutral fats or polyethylene glycol or derivatives thereof.

The compounds according to the invention can be administered for prophylaxis and for therapy of breast cancer or prostate cancer or endometriosis in combination with one or more of the following active ingredients:

1) Antiandrogens, such as cyproterone acetate, flutamide, casodex, etc.

2) Gonadotropin hormone (GnRH) agonists such as synarel, lupron, busrelin

3) Aromatase inhibitors such as anastrozole, formestane, letrozole, exemestane 4) 5α-Reductase inhibitors, such as finasteride 5) Cytostatic agents, such as vinblastine, daunorubicin 6) VEGF-kinase inhibitors 7) Antigestagens, such as onapristones, mifepristones 8) Antiestrogens such as tamoxifen 9) Antisense oligonucleotides 10) EGF Antibodies Moreover, the compounds of general formula I according to the invention can be used for therapy and prophylaxis of other pathological conditions that are not mentioned above.

The following examples are used for a more detailed explanation of the subject of the invention, without intending that it be limited to these examples.

Starting from the 17-keto derivatives, 17-oxiranes (M. Hübner, I. Noack, *J. prakt. Chem.* 1972, 314, 667), and the corresponding 17a-homo derivatives therefrom (M. Hübner, K. Ponsold, *Z. Chem.* 1982, 22, 186) can be produced. The above-mentioned reaction steps can be performed before or after functionalization of the 2-position.

The introduction of halogens in 2-position is carried out by means of orthothallation as described in the literature for 17-keto derivatives (P. C. Bulman Page et al., *Tetrahedron* 1990, 46, 2059).

The functionalization of the C atom 2 of an estra-1,3,5(10)-trien-17-one derivative is preferably carried out by Friedel-Crafts acylation as described in the literature (T. Nambara et al., *Chem. Pharm. Bull.* 1979, 18, 474). After alteration of the protective group in 3-position, a 2-carboxy-estra-1,3,5(10)-trien-17-one is generated by Baeyer-Villiger oxidation (M. B. Smith, J. March, *March's Advanced Organic Chemistry*, 5$^{th}$ Edition, Wiley Sons 2001, 1417-1418). The ester is saponified and converted with the corresponding alkyl halide under basic conditions into a 2-alkyl-ether. The cleavage of the protective group in 3-position is carried out as described in the literature (T. W. Greene, P. G. M. Wuts, *Protective Groups in Organic Synthesis*, Wiley & Sons, 1999, 249-275). This process or others (P. N. Rao, J. W. Cessac, *Steroids* 2002, 67, 1065) can be used in accordance with the 17a-homo derivatives.

The corresponding 2-alkyl derivatives can be produced from the 2-acyl derivatives by reduction with sodium borohydride, hydrogenation and subsequent Oppenauer oxidation (C. Djerassi, *Org. React.* 1951, 6, 207).

The introduction of the 2-allyl group can be carried out via a Claisen rearrangement as described in the literature (L. Troisi et al., *Tetrahedron Lett.* 1999, 40, 1771). It can be further functionalized below analogously to the methods that are described by T. Buskas et al. (*J. Org. Chem.* 2000, 65, 958).

Longer, also unsaturated or functionalized alkyl radicals in 2-position can be obtained via the Sonogashira coupling of more suitable, optionally correspondingly protected alkines and subsequent (partial) hydrogenation.

The 17-fluorination of the 17a-ketone can be performed as described by A. C. Stalford et al. (*Steroids* 1997, 62, 750) or else S. Stavber et al. (*Synthesis* 2002, 2609).

The synthesis of 16,17-dehydro derivatives can also be performed analogously to known processes (see, e.g., P. N. Rao et al., *Steroids* 2002, 67, 1079).

Production Process

EXAMPLE 1

2-Methoxy-17a-oxo-17a-homoestra-1,3,5(10)-trien-3-ol 1

3.61 g of 17α-azidomethyl-3,17β-dihydroxy-2-methoxy-estra-1,3,5(10)-triene and 7.5 g of sodium iodide were suspended in 250 ml of acetonitrile and slowly mixed at room temperature with 15 ml of trimethyl silyl chloride. After 4 hours, another 4 ml of trimethyl silyl chloride was added, and after another 2.5 hours, it was mixed with saturated sodium thiosulfate solution and water and extracted with dichloromethane (3×). The combined organic phases were washed with aqueous sodium bicarbonate solution, dried and concentrated by evaporation in a rotary evaporator. Flash chromatography (cyclohexane/ethyl acetate=10:1→7:1→5:1) yielded 2.12 g (67%) of 2-methoxy-17a-oxo-17a-homoestra-1,3,5(10)-trien-3-ol 1 as colorless crystals.

$^1$H-NMR (CDCl$_3$): δ=1.13 (s, 3H; 18-CH$_3$), 2.62-2.71 (m, 1H; 17-H), 2.77 (dd, 2H; 6-CH$_2$), 3.86 (s, 3H; 2-OCH$_3$), 5.48 (s, 1H; 3-OH), 6.63, 6.78 (2s, 2H; 1-H, 4-H).

EXAMPLE 2

2-Chloro-17a-oxo-17a-homoestra-1,3,5(10)-trien-3-ol 2

307 mg (851 μmol) of 3-acetoxy-2-chloro-17a-oxo-17a-homoestra-1,3,5(10)-triene was dissolved in 24 ml of dichloromethane/methanol (2:1) and mixed with 45 mg of sodium methanolate. After 1.5 hours, it was neutralized with Amberlite IR120 (H+), filtered, and concentrated by evaporation in a rotary evaporator. Flash chromatography (toluene/ethyl acetate=25:1) yielded 173 mg (64%) of 2-chloro-17a-oxo-17a-homoestra-1,3,5(10)-trien-3-ol 2 as colorless crystals.

$^1$H-NMR (CDCl$_3$): δ=1.12 (s, 3H; 18-CH$_3$), 2.62-2.82 (m, 2H; 17-H, 6-CH$_2$), 5.39 (s, 1H; 3-OH), 6.72, 7.21 (2s, 2H; 1-H, 4-H).

EXAMPLE 3

2-Bromo-17a-oxo-17a-homoestra-1,3,5(10)-trien-3-ol 3

3 was produced analogously to the method, described for 17-keto derivatives, by P. C. Bulman Page et al., *Tetrahedron* 1990, 46, 2059.

$^1$H-NMR (CDCl$_3$): δ=1.12 (s, 3H; 18-CH$_3$), 2.62-2.82 (m, 2H; 17-H, 6-CH$_2$), 5.41 (s, 1H; 3-OH), 6.73, 7.34 (2s, 2H; 1-H, 4-H).

EXAMPLE 4

2-Iodo-17a-oxo-17a-homoestra-1,3,5(10)-trien-3-ol 4

4 was produced analogously to the method, described for the 17-keto derivatives, by P. C. Bulman Page et al., *Tetrahedron* 1990, 46, 2059.

$^1$H-NMR (CDCl$_3$): δ=1.12 (s, 3H; 18-CH$_3$), 2.62-2.71 (ddd, J=6.8, 14.1, 14.1 Hz, 1H; 17-H), 2.77-2.81 (m, 2H; 6-CH$_2$), 5.29 (s, 1H; 3-OH), 6.71, 7.52 (2s, 2H; 1-H, 4-H).

EXAMPLE 5

2-Chloro-17α-fluoro-17a-oxo-17a-homoestra-1,3,5(10)-trien-3-ol 5a and 2-Chloro-17β-fluoro-17a-oxo-17a-homoestra-1,3,5(10)-trien-3-ol 5b 60 mg (188 μmol) of 2-chloro-17a-oxo-17a-homoestra-1,3,5(10)-trien-3-ol 2 was refluxed with about 190 mg of 1-fluoro-4-hydroxy-1,4-diazonia-bicyclo[2,2,2]-octane bis (tetrafluoroborate) on aluminum oxide in 10 ml of methanol for 5 hours, cooled to room temperature, mixed with 1N hydrochloric acid and extracted with dichloromethane. The organic phases are dried and concentrated by evaporation in a rotary evaporator. Purification by means of HPLC (Chiracel OJ-H, n-heptane/2-propanol=6:4) yielded about 10 mg each of 2-chloro-17β-fluoro-17a-oxo-17a-homoestra-1,3,5(10)-trien-3-ol 5a and 2-chloro-17β-fluoro-17a-oxo-17a-homoestra-1,3,5(10)-trien-3-ol 5b as colorless solids.

5a: $^1$H-NMR (CDCl$_3$): δ=1.13 (s, 3H; 18-CH$_3$), 5.32 (ddd, J$_{HF}$=48.8, J$_{HH}$=7.4, 12.5 Hz, 1H; 17β-H), 6.72, 7.21 (2 s, 2H; 1-H, 4-H)—$^{19}$F-NMR (CDCl$_3$): δ=−192.20 (dd, J=48.9, 12.8 Hz). 5b: $^1$H-NMR (CDCl$_3$): δ=1.21 (d, J=3.1 Hz, 3H; 18-CH$_3$), 4.86 (ddd, J$_{HF}$49.2, J$_{HH}$=3.9, 6.6 Hz, 1H; 17α-H), 6.73, 7.20 (2s, 2H; 1-H, 4-H)—$^9$F-NMR (CDCl$_3$): δ=−183.02−−183.28 (m).

EXAMPLE 6

2-(2-Phenylethyl)-17a-oxo-17a-homoestra-1,3,5(10)-trien-3-ol 6

56 mg (123 μmol) of 3-acetoxy-2-iodo-17a-oxo-17a-homoestra-1,3,5(10)-triene was dissolved in 8 ml of triethylamine/THF (3:1), mixed with 3 mg of palladium(II) acetate, 5 mg of copper(I) iodide, 6.5 mg of triphenylphosphine and 26 μl of phenyl-acetylene, and stirred for 45 minutes at room temperature under argon. Then, it was diluted with ethyl acetate, washed with 1N hydrochloric acid, saturated sodium bicarbonate solution and common salt solution, dried, concentrated by evaporation in a rotary evaporator, and purified by flash chromatography (cyclohexane/ethyl acetate 10:1→5:1). 42 mg (80%) of 3-acetoxy-2-(2-phenylethinyl)-17a-oxo-17a-homoestra-1,3,5(10)-triene was obtained as brown-black crystals.

$^1$H-NMR (CDCl$_3$): δ=1.12 (s, 3H; 18-CH$_3$), 2.35 (s, 3H, COCH$_3$), 6.82, 7.50 (2s, 2H; 1-H, 4-H), 7.31-7.48 (m, 5H; Ph)—$^{13}$C-NMR (CDCl$_3$): δ=16.79, 20.84, 22.87, 25.59, 25.80, 26.22, 29.75, 32.33, 37.08, 38.14, 42.89, 48.17, 50.17, 84.58, 92.92, 114.101, 121.64, 122.91, 128.12, 129.82, 131.24, 137.92, 138.52, 148.90, 168.97, 215.83.

27 mg (63 μmol) of 3-acetoxy-2-(2-phenylethinyl)-17a-oxo-17a-homoestra-1,3,5(10)-triene was dissolved in 10 ml of ethyl acetate/THF (9:1), mixed with 3 drops of acetic acid and 55 mg of palladium on activated carbon (10%), and hydrogenated for 3 hours. Then, the catalyst was filtered off, concentrated by evaporation in a rotary evaporator, and co-evaporated several times with toluene. The residue was dissolved in 6 ml of dichloromethane, mixed with 20 ml of methanol and 100 mg of sodium methanolate, and stirred for 2 hours. Then, it was neutralized with Amberlite IR120 (H+), filtered and concentrated by evaporation in a rotary evaporator. Flash chromatography (cyclohexane/ethyl acetate=5:1) yielded 16 mg (65%) of 2-(2-phenylethyl)-17a-oxo-17a-homoestra-1,3,5(10)-trien-3-ol 6 as colorless needles.

$^1$H-NMR (CDCl$_3$): δ=1.13 (s, 3H; 18-CH$_3$), 2.85-2.89 (m, 4H, PhCH$_2$), 4.46 (s, 1H; OH), 6.48, 7.02 (2s, 2H; 1-H, 4-H), 7.19-7.30 (m, 5H; Ph).

EXAMPLE 7

2-Allyl-17a-oxo-17a-homoestra-1,3,5(10)-trien-3-ol 7

315 mg (1.11 mmol) of 17a-oxo-17a-homoestra-1,3,5(10)-trien-3-ol was dissolved in 5 ml of absolute DMF, mixed with 1.8 g of cesium carbonate and 1 ml of allyl bromide and heated for 3 hours to 60° C. Then, it was mixed with ethyl acetate and washed with water and common salt solution. The organic phase was separated, dried, and concentrated by evaporation in a rotary evaporator. Flash chromatography (cyclohexane/ethyl acetate=40:1→20:1→10:1) yielded 322 mg (89%) of 3-allyloxy-17a-oxo-17a-homoestra-1,3,5(110)-triene as colorless crystals.

$^1$H-NMR (CDCl$_3$): δ=1.12 (d, 3H; 18-CH$_3$), 2.62-2.71 (m, 1H; 17-H), 2.83-2.86 (m, 2H; 6-H), 4.50 (d, J=5.0 Hz, 2H; OCH$_2$), 5.26 (dd, J=1.2, 10.5 Hz, 1H, =CHH), 5.37 (dd, J=1.2, 17.2 Hz, 1H; =CHH), 5.99-6.07 (m, 1H; CH=CH$_2$), 6.63 (d, J=2.3 Hz, 1H; 4-H), 6.72 (dd, J=2.3, 8.2 Hz, 1H; 2-H), 7.20 (d, J=8.6 Hz, 1H; 1-H).

315 mg (971 μmol) of 3-allyloxy-17a-oxo-17a-homoestra-1,3,5(10)-triene was dissolved in 25 ml of diethylaniline under argon and refluxed for 8 hours. Then, it was mixed with ethyl acetate and washed with 1N hydrochloric acid and common salt solution. The organic phase was separated, dried, and concentrated by evaporation in a rotary evaporator. Flash chromatography (cyclohexane/ethyl acetate=9:1) yielded 312 mg (99%) of a mixture of the two regioisomers as colorless foam. Separation by means of HPLC (Chirapak AD-H, n-heptane/2-propanol=8:2) yielded 108 mg of 2-allyl-17a-oxo-17a-homoestra-1,3,5(10)-trien-3-ol 7 as colorless crystals.

$^1$H-NMR (CDCl$_3$): δ=1.12 (d, 3H; 18-CH$_3$), 2.62-2.71 (m, 1H; 17-H), 2.78-2.82 (m, 2H; 6-H), 3.37 (d, J=6.3 Hz, 2H; OCH$_2$CH=), 4.89 (s, 1H; OH), 5.12-5.18 (m, 2H, =CH$_2$), 5.94-6.05 (m, 1H; CH=CH$_2$), 6.54, 7.02 (2s, 2H; 1-H, 4-H).

EXAMPLE 8

2-Bromo-17a-oxo-17a-homoestra-1,3,5(10),16-tetraen-3-ol 8

$^1$H-NMR (CDCl$_3$): δ=1.05 (d, 3H; 18-CH$_3$), 2.62-2.71 (m, 1H; 17-H), 5.95 (dd, J=2.5, 10.0 Hz, 1H; =CH), 6.87-6.91 (m, 1H, =CH), 6.74, 7.36 (2s, 2H; 1-H, 4-H)—$^{13}$C-NMR (CDCl$_3$): δ=15.63, 25.64, 25.85, 27.13, 29.28, 32.08, 38.81, 42.34, 44.45, 45.32, 107.42, 115.37, 127.56, 128.61, 133.76, 137.46, 147.25, 149.79, 205.04.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2004 032 673.8, filed Jul. 2, 2004, and U.S. Provisional Application Ser. No. 60/584,475, filed Jul. 2, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 2-substituted D-homo-estratriene compound of formula I

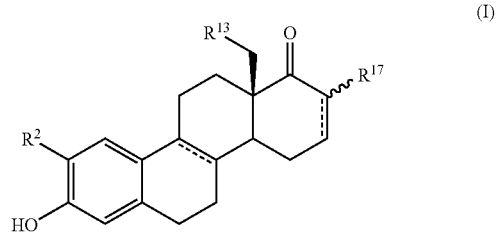

in which

R$^2$ means an aralkyl or an alkylaryl radical, wherein the aryl portion of the aralkyl or alkylaryl radical is a: phenyl; 1- or 2-naphthyl; 2-, 3-, or 4-pyridinyl; 2- or 3-furyl;

2- or 3-thienyl; 2- or 3-pyrrolyl; 2-, 4- or 5-imidazolyl; pyrazinyl; 2,4- or 5-pyrimidinyl; or 3- or 4-pyridazinyl radical, each optionally substituted by methyl, ethyl, trifluoromethyl, pentafluoroethyl, trifluoromethylthio, methoxy, ethoxy, nitro, cyano, halogen, hydroxy, amino, mono($C_{1-8}$-alkyl), di($C_{1-8}$-alkyl)amino where the alkyl groups are identical or different, or di(aralkyl)amino where the aryl portion of aralkyl is as identified here and where the aralkyl groups are identical or different, $R^{13}$ means a hydrogen atom or a methyl group, $R^{17}$ means a hydrogen atom or a fluorine atom, whereby the dotted lines in each of the B- and D-ring of the steroid molecule mean optional additional double bonds, or a pharmaceutically acceptable salt thereof.

2. A 2-substituted D-homo-estratriene compound according to claim 1, wherein $R^{13}$ is a hydrogen atom.

3. A 2-substituted D-homo-estratriene compound according to claim 1, which is 2-(2-Phenylethyl)-17a-oxo-17a-homoestra-1,3,5(10)-trien-3-ol.

4. A pharmaceutical composition that comprises at least one compound of formula I according to claim 1 and a pharmaceutically compatible adjuvant and/or vehicle.

5. The pharmaceutical composition of claim 4, wherein the composition further comprises at least one additional active ingredient.

6. The pharmaceutical composition of claim 5, wherein the at least one additional active ingredient is an antiandrogen, antigestagen, aromatase inhibitor or an antiestrogen.

7. The pharmaceutical composition of claim 4, wherein the composition is provided in a daily dose form containing 5 μg to 50 mg, per kg body weight of the intended patient, of the at least one compound of formula I.

8. A method for preparing a medicament which comprises at least one compound of formula I according to claim 1, wherein the method comprises formulating at least one compound of formula I into a suitable medicament form.

9. A method for treating an estrogen-dependent disease that can be positively influenced by the inhibition of the 17β-hydroxy steroid dehydrogenase wherein the disease is selected from breast cancer, prostate cancer and endometriosis, which comprises administering to a patient in need thereof a 17β-hydroxy steroid dehydrogenase inhibiting effective amount of a 2-substituted D-homoestra-1,3,5(10)-triene compound according to claim 1.

10. The method of claim 9, wherein the at least one compound of formula I is administered in a daily dose of 5 μg to 50 mg per kg of body weight of the patient.

11. The method of claim 9, wherein the at least one compound of formula I is administered in a daily dose of 10 μg to 30 mg per kg of body weight of the patient.

12. The method of claim 9, which further comprises administering to the patient at least one additional active ingredient.

13. The method of claim 12, wherein the at least one additional active ingredient is an antiandrogen, antigestagen, aromatase inhibitor or an antiestrogen.

* * * * *